United States Patent [19]

Levy

[11] Patent Number: 5,021,407

[45] Date of Patent: * Jun. 4, 1991

[54] TETRACYCLINE ACTIVITY ENHANCEMENT

[75] Inventor: Stuart B. Levy, Boston, Mass.

[73] Assignee: Trustees of Tufts College, Boston, Mass.

[ * ] Notice: The portion of the term of this patent subsequent to Feb. 21, 2006 has been disclaimed.

[21] Appl. No.: 850,843

[22] Filed: Apr. 11, 1986

Related U.S. Application Data

[63] Continuation of Ser. No. 442,688, Nov. 18, 1982, abandoned.

[51] Int. Cl.$^5$ ............................................. A01N 37/18
[52] U.S. Cl. ..................................... 514/154; 514/152
[58] Field of Search ................. 424/116, 117; 514/152

[56] References Cited

U.S. PATENT DOCUMENTS

| | | | |
|---|---|---|---|
| 3,454,697 | 7/1969 | Joyner et al. | 514/152 |
| 4,024,272 | 5/1977 | Rogalski et al. | 514/152 |
| 4,126,680 | 11/1978 | Armstrong | 514/152 |

OTHER PUBLICATIONS

Grassi et al., *New Trends in Antibiotics: Research & Therapy*, pp. 3–54 (1981).
Chem. Abst. 89:71494n (Connamacher et al.).
Chem. Abst. 90:198211u (Samra et al.).
Chem. Abst. 83:1393f (Candanaza et al.).
Chem. Abst. 81:115200e (Leigh et al.).
Chem. Abst. 82:26560(a) (Lebek et al.).
Chem. Abst. 74:74941g (Kuck et al.).
Chem. Abst. 79:74181n (Kuck et al. I).
Chem. Abst. 86:150977p (Williams et al.).
Chem. Abst. 79:143198n (Sompolinsky et al.).
Levy, S. B. "The Tetracyclines: Microbial Sensitivity and Resistance," *New Trends in Antibiotics: Research and Therapy*, Elsevier/North-Holland Biomedical Press, 1981, pp. 27–44.
Chapra et al., "The Tetracyclines: Prospects at the Beginnin of the 1980's," *Journal of Microbial Chemotherapy*, 8:5–21 (1981).
Lehninger, *Biochemistry—The Molecular Basis of Cell Structure and Function* (2 ed., Worth Publishers, 1975) p. 941.
Mendez, B. et al., "Heterogeneith of Tetracyclines; Resistance, Determinants," Plasmid, 3:99–108 (1980).
Levy and McCurry, "Detection of an Inducible Membrane Protein Associated with R–Factor Mediated Tetracycline Resistance," Biochemical and Biophysical Research Commun. 56(4):1060–1068 (1974).
Levy and McCurry, "Plasmid–Determined Tetracycline Resistance Involves New Transport Systems for Tetracycline," *Nature*, 275 (5683): 90–92 (1978).
McCurry and Levy, "Two Transport Systems for Tetracycline in Sensitive *Escherichia coli*: Critical Role for an Initial Rapid Uptake System Insensitive to Energy Inhibitors", Antimicrobial Agents and Chemotherapy 14(2):201–209 (1978).
McCurry et al., "Active Efflux of Tetracycline Encoded by Four Genetically Different Tetracycline Resistance Determinants in *Escherichia coli*," Proc. Nat. Acad. of Sci., U.S.A., 77(7):3975–3977 (1980).
Curiale and Levy., "Two Complementation Groups Mediate Tetracycline Resistance Determined by Tn10", *Journal of Bacteriology*, 151(1); 209–215 (1982).
Korolkovas, A. et al., *Essentials of Medicinal Chemistry* (John Wiley & Sons, Inc., 1976) at 512–517.
"Active Uptake of Tetracycline by Membrane Vesicles from Susceptible *Escherichia coli*", *Antimicrobial Agents and Chemotherapy*, 20(3):307–313 (1981).
Brock et al., "Comparison of the In Vitro Serum Microbiological Activity of a Triple Tetracycline Tablet, 300 mg B.I.D. with Oxytetracycline, 250 mg Q.I.D.", *J. Int. Med. Res.* (1981), 9,360.

*Primary Examiner*—Frederick E. Waddell
*Assistant Examiner*—Criares
*Attorney, Agent, or Firm*—Gregory D. Williams; David G. Conlin

[57] ABSTRACT

Methods and products for overcoming bacterial resistance to tetracycline-type antibiotics by inhibiting the plasmid-mediated active efflux system for tetracycline in the resistant bacterial cell by administering with tetracycline efflux system blocking agents, thereby increasing the sensitivity of the resistant cell to tetracycline-type antibiotics.

12 Claims, No Drawings

TETRACYCLINE ACTIVITY ENHANCEMENT

This is a continuation of co-pending application Ser. No. 442,668 filed on Nov. 18, 1982 now abandoned.

FIELD OF THE INVENTION

This invention relates to methods and products for enhancing the effectiveness of antibiotics, more particularly, to methods and products for overcoming bacterial resistance to antibiotics of the tetracycline family.

BACKGROUND OF THE INVENTION

The tetracyclines are bacteriostatic antibiotics used to treat a broad spectrum of microbial disease agents in humans, animals and plants.

Many bacteria are able to adapt to their environment in ways which permit them to become resistant to antibiotics. Strains of group A streptococci devoloped resistance to sulfadiazine during World War II. Resistant staphylococcal infections began to spread through public institutions and hospitals following the widespread use of penicillin. Since the introduction of tetracyclines into clinical practice, a number of microorganisms have developed resistance to these drugs. Treatment of bacterial infections in palm trees with tetracycline solutions through the root system has become increasingly ineffective. See Levy, "The Tetracyclines: Microbial Sensitivity and Resistance," *New Trends in Antibiotics: Research and Therapy*, Elsevier/North-Holland Biomedical Press, 1981, pp. 27-44; Chopra et al., "The tetracyclines: prospects at the beginning of the 1980's," *Journal of Antimicrobial Chemotherapy*, 8:5-21, (1981,) which are incorporated herein by reference.

Tetracycline was one of the real wonder drugs when introduced into the clinical world in 1948. However, many microorganisms have developed resistance to tetracycline. More alarming is the emergence of organisms with resistance to the newer tetracycline analogs. Resistant bacteria are also appearing among individuals who have not consciously ingested the drug. It has therefore become increasingly important to determine the mode of resistance and to develop a method of circumvention. Since the mechanism does not degrade the drug and breakdown in nature is small, tetracycline remains in the environment to continue to promote emergence of resistant organisms. Thus determination of a method that would overcome this resistance would provide a substantial increase in the effectiveness of tetracyclines, while reducing the present large increase in tetracycline resistant microbial diseases.

Investigations into the mode of action of the tetracyclines support observations that the tetracyclines inhibit the protein synthesis of sensitive bacteria at the level of the ribosome, as described in Lehninger, *Biochemistry—The Molecular Basis of Cell Structure and Function*, (2d ed., Worth Publishers, 1975), p. 941, which is incorporated herein by reference. This inhibition interferes with total protein synthesis and biosynthesis of the bacterial respiratory system.

In the resistant organism, resistance does not promote inactivation of the tetracycline molecule. Rather, the total efflux rate is increased and the steady state accumulation by the cell is obtained at a lower, biologically ineffective concentration of drug.

Resistance to the tetracyclines in most bacterial species is specified by extra-chromosomal, autonomously replicating and often transmissible plasmids, called R factors, which carry genes which mediate tetracycline resistance. Two kinds of tetracycline resistance determinants among plasmids have been described: those with resistance to tetracycline alone and those with resistance to tetracycline and its lipophilic analogs. It has been shown that at least four different genetic elements encode the tetracycline resistance phenotype. See Mendez et al., "Heterogeneity of Tetracycline Resistance Determinants," *Plasmid*, 3:99-108, 1980, which is incorporated herein by reference.

Plasmid mediated resistance is inducible in many bacteria. The resistance level can be experimentally increased by preincubation of the cells in subinhibitory amounts of tetracycline. It was found that coincident with induced resistance was the induced synthesis of a plasmid-encoded inner membrane protein, which was designated "TET" protein. See Levy and McMurry, "Detection of an Inducible Membrane Protein Associated with R-Factor-Mediated Tetracycline Resistance." *Biochemical and Biophysical Research Communications*, 56(4):1060-68, (1974), which is incorporated herein by reference. Moreover, accumulation of drug by resistant cells was dramatically different from that accumulation in sensitive cells. See Levy and McMurry, "Plasmid-determined Tetracycline Resistance involves new transport systems for tetracycline," *Nature*, 275 (5683): 90-92 (1978), which is incorporated herein by reference. While tetracycline was actively accumulated by sensitive cells (McMurry and Levy in "Two transport systems for Tetracycline in Sensitive *Escherichia coli*: Critical role for an Initial Rapid Uptake System Insensitive to Energy Inhibitors," *Antimicrobial Agents and Chemotherapy* 14(2); 201-09 (1978), which is incorporated herein by reference), these uptake systems were found to be altered by at least one tetracycline resistance plasmid, R222. *Nature* 275 (5683), supra, at 91. They subsequently demonstrated that all four plasmid-borne tetracycline resistance determinants specified an active efflux system for tetracycline, (McMurry et al., "Active Efflux of Tetracycline Encoded by Four Genetically Different Tetracycline Resistance Determinants in *Escherichia coli*," *Pro. Nat. Acad. of Sci. U.S.A.* 77 (7): 3974-77 (1980), which is incorporated herein by reference). More recently, using tetracycline sensitive mutations which mapped in the TET structural region, the investigators demonstrated two genetic-complementation groups designated TET A and TET B. Absence of either one of these gene loci causes loss of the energy-dependent efflux of tetracycline which is characteristic of tetracycline resistance. (Curiale and Levy, "Two Complementation Groups Mediate Tetracycline Resistance Determined by Tn10," *Journal of Bacteriology*, 151(1): 209-15 (1982), which is incorporated herein by reference.)

It is among the objects of the present invention to provide a process for enhancing the bacteriostatic and bacteriocidal effects of the tetracyclines. It is also an object to provide a process for circumventing the tetracycline efflux mechanism of resistant bacterial cells. It is also an object to provide a process for promoting accumulation of minimum inhibitory concentrations of tetracyclines within the bacterial cell. It is also an object to provide a process for converting a tetracycline resistant cell into a tetracycline sensitive cell. Additional objects and advantages of the invention will be set forth in part in the description which follows, and in part will be obvious from the description, or may be learned by practice of the invention. The objects and advantages of the invention may be realized and obtained by means of the instrumentalities and combinations particularly pointed out in the appended claims.

SUMMARY OF THE INVENTION

The invention herein comprises methods and products for inhibition of the function of the plasmid-mediated active efflux system for tetracycline-type antibiotics in the bacterial cell, wherein tetracycline-type antibiotics are administered to the cell in combination with tetracycline efflux system inhibitory or blocking agents. The active efflux system in resistance cells is thus inhibited, and the tetracycline type antibiotic is effective at lower concentration to terminate cellular protein synthesis in previously tetracycline-resistant microorganisms. The use of such combinations provides a process for enhancing the bacteriocidal and bacteriostatic effects of the tetracyclines. When the efflux system of the resistance cell is blocked, the resistant cell converts to sensitive cell characteristics.

DETAILED DESCRIPTION OF THE INVENTION

In accord with the present invention, a method of blocking the tetracycline efflux system of tetracycline resistant cells is obtained by treating tetracycline resistant cells with an efflux blocking agent, i.e., a tetracycline analog or another type of agent which interferes with the action of the TET A and/or TET B proteins or protein domains and thus decreases efflux of tetracyclines from the cell. This method renders formerly resistant cells non-resistant, i.e., sensitive to tetracycline. Inhibition of the tetracycline efflux system may be demonstrated by a comparison of the transport of tetracycline with and without an efflux blocking agent by susceptible cells and by resistant cells. Preferably, tetracycline type antibiotics are administered in conjunction with, or shortly after treatment with the efflux blocking agent.

By "tetracycline-type antibiotic", tetracyclines, or the tetracycline family, as used herein, is meant tetracycline and its analogs, which are compounds having the structural formula:

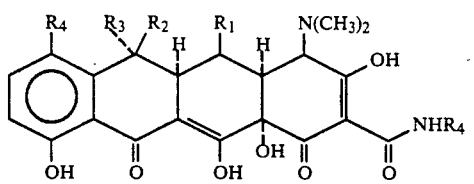

wherein $R_1$ to $R_5$ may be hydrogen, hydroxy, alkyl, substituted alkoxy, alkylene, halogen, etc. See Korolkovas et al., *Essentials of Medicinal Chemistry* (John Wiley & Son, Inc., 1976), at 512-17, the disclosure of which is incorporated herein by reference. Preferably $R_1$ and $R_2$ are hydrogen or hydroxy, $R_3$ is hydrogen or methyl, $R_4$ is hydrogen, halogen, preferably chlorine, or amino, preferably dimethylamino, and $R_5$ is hydrogen, N-methyl pyrole, (as in rolitetracycline) or

(as in lymecycline). $R_2$ and $R_3$ together may be methylene, as in methacycline.

In tetracyline sensitive cells, tetracycline is accumulated so that the intracellular concentration of tetracyclines exceeds the extracellular level. Part of the uptake occurs via an initial energy-independent phase of antibiotic uptake as detailed in *Antimicrobial Agents* 14(2), supra at 201. However, at least half of the uptake occurs via an energy dependent system sensitive to metabolic inhibitors.

In resistant organisms, an additional energy-demanding and carrier-mediated active efflux system is incorporated by the presence of resistance-determinator genetic material, such as a TET resistant gene encoded by a plasmid. Resistance does not occur by means of inactivation of the tetracycline molecule. Rather the total efflux rate is increased, so that, at a steady state, the resistant organism has a low intracellular level of tetracycline. This resistance mechanism is an active system for pumping the drug out of the cell.

We have now found that efflux of tetracycline type antibiotics can be blocked by use of a blocking agent which binds, associates with, or otherwise deactivates the carrier protein(s) which are active in effluxing tetracyclines from the cell. While not wishing to be bound by theory, it is believed that the proteins or protein domains known as TET A and TET B, or other similar carrier proteins, e.g. from other tetracycline resistance determinants, actively instill resistance in microorganisms by binding to or otherwise associating with the tetracycline type antibiotic and transporting the antibiotic out of the cell. It further appears that both TET A and TET B proteins or protein domains have a critical and supportive role in affecting the efflux system, and thus it is possible to block the efflux system and convert resistant microorganisms to sensitive microorganisms, by use of a blocking agent which binds or associates with either TET A and/or TET B proteins.

In accord with the present invention, the preferred blocking agents are analogs or derivatives of tetracyclines, or compounds which contain a sufficient part of the tetracycline structure such that they are recognized by and bound to or otherwise associated with at least one of the carrier protein molecules or domains which are responsible for effluxing tetracycline-type antibiotics, and thus are efficient in disrupting the efflux system of the microorganism involved. Suitable blocking agents include but are not limited to the known tetracycline antibiotics, including oxytetracycline, chlorotetracycline, demeclocycline, doxycycline, B-chelocardin, minocycline, rolitetracycline, lymecycline, sancycline and methacycline, and other compounds including latent forms of tetracycline, such as apicycline, clomocycline, guamecycline, meglucycline; mepycycline, penimepicycline, pipacycline, etamocycline, penimocycline, etc. Tetracycline(s) may also be used in salt form, e.g. as a tetracycline lactate, t. lauryl sulfate, t. phosphate complex, t. cyclohexyl sulfamate, or other pharmaceutically acceptable salts.

The amount of blocking agent to be used varies with the efficiency of its blocking activity, its absorption by the organism being treated, and the degree of resistance of the microorganism. Sufficient amounts of the blocking agent should be used to make the microorganism susceptible to a pharmaceutically acceptable level of tetracycline in the man, animal or plant being treated. The molar ratio of blocking agent to tetracycline or tetracycline type antibiotic which is administered may generally be from 0.01 to 100, preferably from 0.05 to 2.0 and more preferably 0.05 to 1.0. In in vivo treatment, the blocking agent may be administered in amounts which are sufficient to exhibit blocking effect, but which do not adversely affect the subject. This does not apply to use of this invention in vitro, e.g., in processing chemical reactions, etc. Generally, the daily dosage of blocking agent for treatment of disease in mammals may range from 0.01 to 100 mg/Kg normal body weight, preferably in an amount of about 0.1 to 50 mg/Kg body weight. The blocking agent may be administered separately from the tetracycline type antibiotic, but preferably is administered simultaneously with the tetracycline type antibiotic. Typically, tetracycline-type antibiotics will be administered in a regular daily course of treatment, to attain and maintain a concentration in the blood or the bodily fluids which will inhibit the microorganism being treated. Since the presence of the blocking agent deactivates the resistance of the microorganism to the tetracycline type antibiotic, the blocking agent should also be utilized in a continuing treatment to render the antibiotic treatment effective.

Non-tetracycline based compounds may be utilized as blocking agents, provided that their structure is such as to interact with the carriers which cause antibiotic efflux so as to prevent or decrease that efflux. The efficiency of blocking agents in reducing efflux of tetracycline type antibiotics can be determined by testing against a tetracycline resistant bacteria. The bacteria used may be naturally occurring tetracycline resistant bacteria, or may be made by incorporating plasmids which code for tetracycline resistance into other bacteria hosts.

Preferably the blocking agent and a tetracycline type antibiotic are combined in a pharmaceutical composition with a pharmaceutically acceptable carrier. The active ingredients may be administered by any route appropriate to the condition to be treated, suitable routes including oral, nasal (e.g., by spray) and parenteral (including subcutaneous, intramuscular and intravenous). It will be appreciated that the preferred route will vary with the condition to be treated.

While it is possible for the blocking agent to be administered as the raw chemical, it is preferable to present it as a pharmaceutical formulation preparation.

The formulations, for veterinary, agricultural and human use, of the present invention comprise the active ingredient, e.g. blocking agent plus tetracycline family drug, as above defined, together with one or more acceptable carriers therefore and optionally other therapeutic ingredients. The carrier(s) must be "acceptable" in the sense of being compatible with the other ingredients of the formulation and not deleterious to the recipient thereof. Desirably the formulation should not include oxidizing agents and other substances with which these antibiotics and their derivatives and blocking agents are known to be incompatible. The formulations include those suitable for oral or parenteral (including subcutaneous, intramuscular and intravenous) administration, although the most suitable route in any given case will depend upon for example, the active ingredient and the condition to be treated. The formulations may conveniently be presented in unit dosage form and may be prepared by any of the methods well known in the art of pharmacy. All methods include the step of bringing into association the active ingredient with the carrier which constitutes one or more accessory ingredients. In general the formulations are prepared by uniformly and intimately bringing into association the active ingredients with liquid carriers or finely divided solid carriers or both, and then, if necessary, shaping the product into the desired formulation.

Formulations of the present invention suitable for oral administration may be presented as discrete units such as capsules, cachets or tablets each containing a predetermined amount of the active ingredient; as a powder or granules; or as a solution or a suspension in an aqueous liquid or a non-aqueous liquid; or as an oil-in-water liquid emulsion or a water-in-oil liquid emulsion. The active ingredient may also be presented as a bolus, nasal spray, suppository, electuary or paste.

A tablet may be made by compression or moulding, optionally with one or more accessory ingredients. Compressed tablets may be prepared by compressing in a suitable machine, the active ingredient in a free-flowing form such as a powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent.

Formulations suitable for parenteral administration conveniently comprise sterile aqueous solutions of the active ingredient which solutions are preferably isotonic with the blood of the recipient. Such formulations may be conveniently prepared by dissolving the active ingredient in water to produce an aqueous solution, and rendering said solution sterile. These formulations may be presented in unit or multi-dose containers, for example sealed ampoules or vials.

It should be understood that in addition to the aforementioned ingredients the formulations of this invention may include one or more additional ingredients such as diluents, buffers, flavouring agents, binders, surface active agents, thickeners, lubricants, preservatives (including anti-oxidants) and the like.

Where the formulation, for human or for veterinary use, is presented in unit dosage form, for example those unit dosage forms specifically mentioned above, each unit thereof conveniently contains the active ingredient (as above defined) in an amount in the range of about 1 mg to about 1000 mg.

To review, a sensitive cell is constantly accumulating tetracycline via an active uptake system and a passive diffusion mechanism. In the resistant cell, there is an active efflux in addition to the active and passive uptake of the drug. The present invention overcomes the problems associated with the plasmid mediated tetracycline resistance by blocking the efflux system with an inhibitor administered in combination with tetracycline analogs. It has been discovered that by blocking the active efflux, the resistant cell accumulates the tetracycline analog just the same as does the sensitive cell.

The present invention teaches that if the efflux system of the resistant cell is blocked, the resistant cell reverts to sensitive cell characteristics. Since the TET proteins are an expression of resistance mediated by the plasmid, blocking the action of the TET A and/or B protein or protein domain(s) will block the action of the efflux system thereby rendering the resistant cell sensitive to tetracycline analogs once again.

The effectiveness of a particular blocking agent can simply be determined by testing for minimum inhibitory concentration (MIC) of the tetracycline type antibiotic of choice, and comparing the MIC of that antibiotic alone, with its MIC when used in combination with the blocking agent. The MIC of the antibiotic or antibiotic blocking agent combination can be determined for example by following the procedure outlined in *Antimicrobial Agents*, 14(2) supra at 202. Other methods of measuring MIC's are well known in the art.

Uptake and/or efflux of tetracycline-type antibiotics or other agents may also be directly measured by counting the amount of radiolabeled drug in whole cells. The advantage of the whole cell method is that transport system saturation can be directly demonstrated. There is a point where the amount of tetracycline influx is greater than simple diffusion or the amount of tetracycline lost via active efflux.

Another method of assaying the effectiveness of blocking agents is the vesicle method, which utilizes everted inner membrane vesicles. *Pro. Nat. Acad. Sci. U.S.A.*, 77(7), supra at 3974–5; McMurry et al., "Active Uptake of Tetracycline by Membrane Vesicles from Susceptible *Escherichia coli*, *Antimicrobial Agents and Chemotherapy* 20(3): 307–13 (1981), which are incorporated herein by reference. Using the everted vesicles, the normal efflux system may be observed as an influx system. The vesicle method has the advantage of measuring competition or binding with the efflux system when increasing amounts of tetracycline-type analogs or other agents are employed.

The following examples are set forth to further illustrate the present invention.

EXAMPLE I

Transport of Minocycline in Susceptible and Resistant *Escherichia coli.*

The invention was demonstrated by use of minocycline, a semisynthetic analog of tetracycline, to interfere with the efflux system of a resistant cell, allowing the formerly tetracycline resistant cell to accumulate tetracycline actively. This example demonstrates that both analogs were effluxed by the same carrier in resistant cells and that by saturating the efflux system with the analog minocycline, tetracycline net efflux from the resistant cell was stopped. The significance of this observation is combined with the further observation that addition of the efflux blocking agent does not affect the active uptake system for tetracycline. Thus, tetracycline continues to accumulate in the resistant cell. The presence of a blocking agent reduces the necessary extracellular concentration of tetracycline to achieve a MIC.

Minocycline is a semisynthetic analog of tetracycline and is much more lipophilic than tetracycline. Plasmids which specify resistance to tetracycline offer much less resistance to its more lipophilic analog minocycline. The level of minocycline resistance is generally 1% to 10% that of tetracycline.

Plasmid R222 contains the class B tetracycline resistance determinant on Tn10. Minocycline resistance of R222 is only 6% of the tetracycline resistance level. Minocycline resistance for another R plasmid, pIP7, which bears the class A tetracycline resistance determinant, is only 1% of the tetracycline resistance level. These plasmids were utilized to compare the transport of the two tetracyclines by susceptible and by two different resistant cells.

In sensitive cells, at low levels of drugs, net actively-accumulated minocycline was about 60 times the external concentration; for tetracycline, the value was 7–8 times the external concentration.

Steady state accumulation of labeled tetracyclines was measured (30 min after addition of label) in resistant cells as a function of external drug concentration in the presence and absence of dinitrophenol. These experiments were identical to those described by McMurry and Levy, supra, *Antimicrobial Agents and Chemotherapy* 14(2) for susceptible cells. Net active efflux was declared if steady-state uptake in the whole cells in the presence of the energy inhibitor DNP was greater than that in its absence.

Normally, addition of energy inhibitors such as DNP or cyanide to resistant cells causes an increase in steady state tetracycline levels, *Nature*, supra, at 90, since active efflux is inhibited in these deenergized cells, *Proc.*, supra at 3974. However, if this efflux were saturated, accumulation in energized cells would no longer be lower. In fact, if resistant cells retained the active uptake system of the host cell (which is unsaturable), this active uptake system might become detectable at external drug levels when the efflux system had been saturated.

Net efflux of tetracycline in cells bearing plasmid R222 was unimpaired even at external tetracycline levels of 1000 $\mu$M. The findings were different with minocycline. While an efflux of minocycline was seen at concentrations less than 6–7 $\mu$M, an active uptake of minocycline was clearly revealed above this level. Above 20 $\mu$M the active uptake was 100 times the external concentration, nearly equal to the 200 fold factor for susceptible cells.

In contrast to these results with R222, cells harboring pIP7, which had a three-fold lower resistance to tetracycline and a twenty-fold lower resistance to minocycline, showed that active tetracycline efflux in cells disappeared at about 5 $\mu$M of tetracycline. As the external level increased, active uptake appeared. However, the amount of tetracycline within the cells remained below that of susceptible cells at the same external concentration (indicating that the tetracycline efflux was not yet saturated) until an abrupt step-up which occurred between 250 and 400 $\mu$M. Active efflux of minocycline in these cells was only below 0.6 $\mu$M. Above this level an active uptake of minocycline was demonstrated.

These results demonstrated that the host-mediated active uptake system for the tetracyclines was retained in resistant cells bearing either type of resistance determinant.

To ascertain whether each of the tetracyclines would interfere with the efflux system of the other, steady-state accumulation was measured of labeled tetracycline in the presence of unlabeled minocycline and vice versa. Cells bearing R222 were used. First, various concentrations of unlabeled minocycline were added with 3.4 $\mu$M [$^3$H] tetracycline. At about 10 $\mu$M unlabeled minocycline, the efflux disappeared, and at higher minocycline levels an active tetracycline uptake was seen. At 200 $\mu$M unlabeled minocycline, the highest concentration tested, the in/out ratio (ratio of internal to external concentration) of energized cells was 50, and of deenergized cells 5. This demonstrated that minocycline was interfering with the tetracycline efflux system.

At about 100 $\mu$M unlabeled tetracycline, efflux of [$^{14}$C] minocycline (at 1.8 $\mu$M) disappeared and an active uptake appeared, indicating that unlabeled tetracycline could also block the active efflux of minocycline. At 400 $\mu$M tetracycline, the highest concentration tested, the in/out ratio of [$^{14}$C] minocycline in energized vs. deenergized cells was 30 and 15 respectively, so the minocycline efflux system had only begun to saturate.

Thus, the efflux of both analogs probably occurred via the same saturable carrier since each analog antagonized the efflux of the other. This finding was further verified by temperature sensitive efflux of both drugs in cells bearing a temperature sensitive tetracycline resistance determinant on R222.

This example has demonstrated that tetracycline and minocycline are accumulated in susceptible cells by both energy-independent and energy-dependent uptake systems. This host-mediated energy-dependent uptake of both analogs was still present in tetracycline-resistant cells. The plasmid-mediated active efflux system previously described for tetracycline also effluxed the more lipophilic analog, minocycline, in resistant cells.

EXAMPLE II

In a similar manner competition experiments have been performed which have demonstrated that another tetracycline analog, chlortetracycline, effectively blocked efflux of minocycline via a cryptic efflux system newly discovered in sensitive *E. coli* cells.

EXAMPLE III

This example demonstrates that the minimum inhibitory concentration of tetracycline could be significantly reduced by the addition of subinhibitory levels of the tetracycline analogs.

In this example, minocycline hydrochloride (received from Lederle Laboratories, N.Y. and described above) and thiatetracycline (received from E. Merck of Darmstadt, Germany), an analog of tetracycline, were employed. The level of thiatetracycline resistance in resistant cells is generally 1% that of tetracycline.

*E. coli* strain D1-209 (described in *Proc. Natl. Acad. Sci.* 77(7), supra at 3974) was employed for this example. Cells used in the uptake experiments were grown from $A_{530}=0.1$ to $A_{530}=0.8$ at 37° C. in Medium A with 0.5% glycerol as previously described. Plasmid bearing cells were induced with 4 µM tetracycline during growth. Cells were washed as previously described. The optical density was then reduced to $10^{-5}$ by dilution of the medium.

Subsequently, one ml of the dilute cellular stock solution was added to tubes containing various analogs and concentrations. The lowest concentration of antibiotic which prevented turbidity starting from an initial inoculum at $A_{530}=10^{-5}$ was designated the minimal inhibitory concentration. The antibiotic concentrations chosen increased in increments of approximately 15% of the magnitude of an initial approximate MIC. Increments began at about 20% of the MIC and terminated at about 200%.

Fresh solutions of drugs at 5 mM for minocycline and thiatetracycline and at 40 mM for tetracycline were prepared weekly and stored at −15° C. Thiatetracycline was dissolved in ethanol. Other chemicals were utilized as described in Example I.

One ml of the stock solution was added to each tube containing various levels of tetracycline to give the final concentrations. The MIC's for the stock solutions at 17.5 hours were 480 µM for tetracycline, 20 µM for minocycline, and 3.5 µM for thiatetracycline. Addition of 4 µM of minocycline to the tetracycline stock solution produced an MIC for tetracycline at 400 µM. Addition of 8 µM of minocycline reduced the MIC of tetracycline to 320 µM. Addition of 0.2 µM thiatetracycline into the tetracycline stock solution did not produce a change from the tetracycline MIC. However, addition of 0.8 µM of thiatetracycline reduced the tetracycline MIC to 300 µM. Therefore, Example III has confirmed the results of Example I by using a subinhibitory concentration of another tetracycline analog in combination with tetracycline.

Thus, it has been demonstrated that the plasmid-mediated tetracycline-resistance efflux system transports more than one kind of tetracycline. Different tetracycline analogs have been demonstrated to have been transported at different rates in Example I. Since tetracycline is being constantly accumulated within the sensitive or resistant cell, it is only necessary to block the efflux system. Similarly, addition of blocking agents such as minocycline and thiatetracycline greatly enhances the effectiveness of tetracyclines on previously resistant microorganisms.

These results are in accord with the scope of this invention, which teaches that if tetracycline-type analogs or other products are administered in combination with tetracycline to tetracycline-resistant cells, the analogs or other factors effectively inhibit the efflux of tetracycline allowing normal accumulation of tetracycline within the cell. In addition, lower concentrations of tetracycline were needed to kill resistant cells when tetracycline was administered in combination with tetracycline analogs. Thus, if the efflux system of the resistant cell is blocked, the resistant cell reverts to sensitive cell characteristics.

I claim:

1. A method of overcoming the resistance of tetracycline resistant bacteria to a tetracycline-type antibiotic, comprising contacting the bacteria with a subinhibitory amount of a blocking agent which interfers with the ability of the bacteria to efflux the antibiotic, wherein the blocking agent is contacted with the bacteria in conjunction with a tetracycline-type antibiotic, the tetracycline-type antibiotic having the structure:

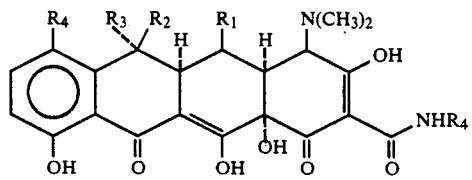

wherein $R_1$ is hydrogen or hydroxy, $R_2$ is hydrogen, hydroxy or, together with $R_3$, is methylene, $R_3$ is hydrogen, methyl, or together with $R_2$, is methylene, $R_4$ is hydrogen, halogen, or amino, and $R_5$ is hydrogen, N-methyl pyrole, or

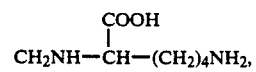

and the blocking agent is a compound which contains a sufficient part of the molecular structure of tetracycline to be bound to at least one of the TET A and TET B proteins, the blocking agent being different from the tetracycline-type antibiotic and employed in an amount which is sufficient to make the bacteria susceptible to a pharmaceutically acceptable amount of the tetracycline-type antibiotic, the blocking agent and antibiotic being employed in a molar ratio of blocking agent to tetracycline-type antibiotic of from about 0.01 to 100.

2. The method of claim 1, wherein the bacteria is contacted with a composition which consists essentially of the blocking agent, the tetracycline antibiotic, and a pharmaceutically acceptable carrier.

3. The method as claimed in claim 2 wherein the tetracycline-type antibiotic is tetracycline.

4. The method as claimed in claim 2 wherein said blocking agent is employed in a concentration sufficient to saturate the active efflux system of the resistant cell.

5. The method as claimed in claim 1 wherein the tetracycline-type antibiotic and blocking agent are administered to a host in need thereof and the molar ratio of said blocking agent to said tetracycline-type antibiotic is from about 0.01 to 100.

6. A method of treatment of tetracycline resistant bacterial infections in animals or plants in need thereof, comprising administering, orally or parenterally, a tetracycline-type antibiotic and a subinhibitory amount of a blocking agent which inhibits the tetracycline efflux system of the bacteria, the tetracycline-type antibiotic having the structure:

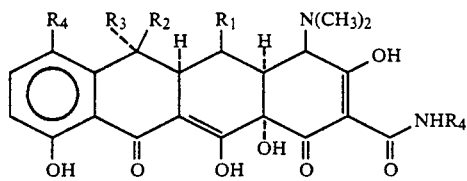

wherein $R_1$ is hydrogen or hydroxy, $R_2$ is hydrogen, hydroxy or, together with $R_3$ is methylene, $R_3$ is hydrogen, methyl, or, together with $R_2$, is methylene, $R_4$ is hydrogen, halogen, or amino and $R_5$ is hydrogen, N-methyl pyrole, or

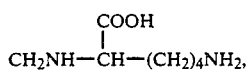

and the blocking agent is a compound which contains a sufficient part of the molecular structure of tetracycline to be bound to at least one of the TET A and TET B proteins, the blocking agent being different from the tetracycline-type antibiotic and employed in an amount which is sufficient to make the tetracycline resistant bacteria susceptible to a pharmaceutically acceptable amount of the tetracycline-type antibiotic, the blocking agent and antibiotic being employed in a molar ratio of blocking agent to tetracycline-type antibiotic of from about 0.01 to 100.

7. The method of claim 1, wherein, the blocking agent is employed in an amount which is sufficient to make the bacteria susceptible to a pharmaceutically acceptable amount of the tetracycline.

8. The method of claim 1, wherein the blocking agent is doxycycline, B-chelocardin, rolitetracycline, lymecycline, sancycline, methacycline, apicycline, clomocycline, guamecycline, meglucycline, mepycycline, penimepicycline, pipacycline, etamocycline or penimocycline.

9. The method of claim 6, wherein te antibiotic and the blocking agent are administered in the form of a composition which consists essentially of the antibiotic, the blocking agent, and a pharmaceutically acceptable carrier.

10. The method of claim 6, wherein the blocking agent is doxycycline, B-chelocardin, rolitetracycline, lymecycline, sancycline, methacycline, apicycline, clomocycline, guamecycline, meglucycline, mepycycline, penimepicycline, pipacycline, etamocycline or penimocycline.

11. The method of claim 6, the blocking agent being employed in an amount of from 0.1 to 100 mg/kg body weight, and the molar ratio of blocking agent to the antibiotic being from about 0.05 to 2.

12. The method of claim 11, wherein the molar ratio of blocking agent to antibiotic is about 0.05 to 1.

* * * * *

UNITED STATES PATENT AND TRADEMARK OFFICE
CERTIFICATE OF CORRECTION

PATENT NO. : 5,021,407

DATED : June 4, 1991

INVENTOR(S) : Stuart B. Levy

It is certified that error appears in the above-identified patent and that said Letters Patent is hereby corrected as shown below:

Title page, col. 1, line 38, "Chapra" should be --Chopra--.
Col. 2, line 3,   "Heterogeneith" should be --Heterogeneity--.
Col. 2, line 5,   "McCurry" should be --McMurry--.
Col. 2, line 9,   "McCurry" should be --McMurry--.
Col. 2, line 12,  "McCurry" should be --McMurry--.
Col. 2, line 17,  "McCurry" should be --McMurry--.
Col. 2, line 26, before "Active Uptake" insert --McMurry, et al.--.
Col. 3, line 49, after "NHR" insert --5--.
Col. 10, line 44, after "NHR" insert --5--.
Col. 11, line 26, after "NHR" insert --5--.
Col. 12, line 22, "te" should be --the--.

Signed and Sealed this

First Day of December, 1992

Attest:

DOUGLAS B. COMER

Attesting Officer

Acting Commissioner of Patents and Trademarks